(12) United States Patent
Ten Kate et al.

(10) Patent No.: US 8,558,021 B2
(45) Date of Patent: Oct. 15, 2013

(54) PROCESS FOR THE CATALYTIC HALOGENATION OF A DIOL

(75) Inventors: Antoon Jacob Berend Ten Kate, Arnhem (NL); Richard Herman Woudenberg, Elst (NL); Eilertdina Henderika Renkema, Renkum (NL); Luc Louis Theophile Vertommen, Westervoort (NL); Carolina Anna Maria Christina Dirix, Westervoort (NL); Tim Baks, Arnhem (NL)

(73) Assignee: Akzo Nobel N.V., Arnhem (NL)

( * ) Notice: Subject to any disclaimer, the term of this patent is extended or adjusted under 35 U.S.C. 154(b) by 105 days.

(21) Appl. No.: 13/256,353

(22) PCT Filed: Mar. 17, 2010

(86) PCT No.: PCT/EP2010/053425
§ 371 (c)(1),
(2), (4) Date: Sep. 13, 2011

(87) PCT Pub. No.: WO2010/106085
PCT Pub. Date: Sep. 23, 2010

(65) Prior Publication Data
US 2012/0004432 A1  Jan. 5, 2012

Related U.S. Application Data

(60) Provisional application No. 61/162,912, filed on Mar. 24, 2009.

(30) Foreign Application Priority Data

Mar. 20, 2009 (EP) .................... 09155759

(51) Int. Cl.
*C07D 301/24* (2006.01)
*C07C 31/34* (2006.01)
(52) U.S. Cl.
USPC ............ 549/521; 549/520; 568/841; 568/844
(58) Field of Classification Search
USPC ........................ 549/521, 520; 568/841, 844
See application file for complete search history.

(56) References Cited

U.S. PATENT DOCUMENTS

| 4,496,753 A | 1/1985 | Kwon et al. |
| 2008/0015369 A1 | 1/2008 | Kruper, Jr. et al. |
| 2008/0015370 A1 | 1/2008 | Hook et al. |
| 2008/0045728 A1 | 2/2008 | Kruper, Jr. et al. |

FOREIGN PATENT DOCUMENTS

| CN | 101215223 | 7/2008 |
| DE | 197308 | 11/1906 |
| DE | 1075103 | 2/1960 |
| EP | 1 059 278 | 12/2000 |
| GB | 2 173 496 | 10/1986 |
| JP | 2009-046437 | * 3/2009 |
| WO | 2005/054167 | 6/2005 |
| WO | 2006/020234 | 2/2006 |
| WO | 2007/144335 | 12/2007 |
| WO | 2009/016149 | 2/2009 |

OTHER PUBLICATIONS

International Search Report issued for PCT/EP2010/053425, dated May 6, 2010, 2 pages.
Organic Syntheses, Coll. vol. 2, p. 256, vol. 16, p. 30, 1943.
Organic Syntheses, Coll. vol. 2, pp. 256-259, 1943.
Organic Syntheses, Coll. vol. 1. pp. 232-235, 1964.
Kirk-Othmer Encyclopedia of Chemical Technology, Third Edition, vol. 9, John Wiley & Son, 1980, pp. 432-471.
Wurtz, A., Compt. Rend., 1859, vol. 48, No. 2, pp. 101-104 (no English translation provided).
McClellan, P. P., "Manufacture and Uses of Ethylene Oxide and Ethylene Glycol", Ind. Eng. Chem., Dec. 1950, vol. 42, No. 12, pp. 2402-2407.
Organic Syntheses, Coll. vol. 8, pp. 434-439, 1993.
Kirk-Othmer Encyclopedia of Chemical Technology, Third Edition, vol. 19, John Wiley & Son, 1982, pp. 246-274.

* cited by examiner

*Primary Examiner* — Taylor Victor Oh
(74) *Attorney, Agent, or Firm* — Kenyon & Kenyon LLP

(57) ABSTRACT

The present invention relates to a process for the catalytic halogenation of an organic compound comprising at least one vicinal diol moiety, said process comprising a step of bringing the organic compound comprising at least one vicinal diol moiety into contact with a hydrogen halide in the presence of a catalyst, characterized in that the catalyst is an organic compound comprising a β-diketone moiety or a β-keto aldehyde moiety.

20 Claims, No Drawings

PROCESS FOR THE CATALYTIC HALOGENATION OF A DIOL

REFERENCE TO RELATED APPLICATION(s)

This application is the U.S. National Phase of PCT/EP2010/053425 filed on Mar. 17, 2010, and claims the benefit of U.S. Provisional Application No. 61/162,912, filed on Mar. 24, 2009.

The present invention relates to a process for the catalytic halogenation of an organic compound comprising at least one vicinal diol moiety by a hydrogen halide in the presence of a suitable catalyst.

Halogenation of organic compounds comprising at least one vicinal diol moiety is an industrially relevant reaction since the resulting products are used in the preparation of epoxides. Epichlorohydrin, for example, which is a widely used precursor to epoxy resins, can be prepared by reacting a dichloropropanol such as 2,3-dichloropropan-1-ol or 1,3-dichloropropan-2-ol with a base. Known processes to prepare dichloropropanol include the chlorination of glycerol using anhydrous hydrochloric acid, in the presence of a catalyst, often a carboxylic acid. DE 197308, for example, describes a process for preparing a chlorohydrin by chlorination of glycerol using anhydrous hydrogen chloride in the presence of an organic acid as the catalyst such as acetic acid, formic acid, propionic acid, cinnamic acid, 1,9-nonanedicarboxylic acid, etc.

JP 2009046437 discloses a process for the preparation of dichloropropanol by reacting glycerol with hydrochloric acid in the presence of a ketone or aldehyde as an alternative for the widely used carboxylic acid catalyst. Examples of catalysts are mentioned to be acetone, methyl ethyl ketone (MEK), acetophenon, and propionic aldehyde.

The catalysts according to JP 2009046437 have reasonable catalytic activity, but for applicability on an industrial scale, a higher catalytic activity would be desirable. Furthermore, these catalysts are relatively volatile. Since generally the product is isolated via distillation, this has the disadvantage that relatively large amounts of catalyst will be drawn off by evaporation together with the product. Moreover, when using for example acetone as the catalyst, the reaction has to be performed under pressure in order to obtain acceptable reaction rates.

Hence, it is an object of the present invention to provide an improved halogenation process wherein a catalyst is used which demonstrates an improved activity and preferably can be used under atmospheric reaction conditions.

It has surprisingly been found that this objective is met if the organic compound comprising at least one vicinal diol moiety is brought into contact with a hydrogen halide in the presence of catalyst which is an organic compound comprising a β-diketone moiety or a β-keto aldehyde moiety.

The skilled person will understand that the keto form of the catalyst is in equilibrium with the enol form (keto-enol tautomerism). It is furthermore noted that the term "an organic compound comprising a β-keto aldehyde moiety" includes malonic aldehyde (propanedial), optionally with one or two alkyl substituents on the bridging carbon atom.

In a particularly preferred embodiment of the present invention, a catalyst is used comprising a β-diketone moiety. Examples thereof include 2,4-pentanedione (which is also denoted as acetylacetone), 1-phenyl-1,3-butanedione (also denoted as 1-benzoylacetone), dibenzoylmethane, 3,5-heptanedione, 1,3-cyclopentanedione, 2,4-hexanedione, and 1,3-cyclohexanedione. It is also possible, however, to use an organic compound comprising more than two carbonyl groups, with at least two of these carbonyl groups being placed in a β-position in relation to each other. Suitable examples of compounds comprising three ketone groups include triacetylmethane, 1,1,2-triacetylethane, 2,4,6-heptanetrione, 1,3,5- and cyclohexanetrione. An example of a suitable tetraketone is 1,1,2,2-tetraacetylethane. Furthermore, it is possible to use a precursor of an organic compound comprising a β-diketone moiety in the halogenation process according to this invention. By the term precursor of an organic compound comprising a β-diketone moiety is meant an organic compound which will provide a β-diketone compound under the halogenation reaction conditions. Suitable examples of such compounds include enol ethers. In a particularly preferred embodiment, a β-diketone-comprising organic compound is used as the catalyst which is not highly sterically hindered. By "highly sterically hindered" we mean that the three carbon atoms attached to the carbonyl groups together comprise three or fewer hydrogen atoms.

In another preferred embodiment a β-diketone moiety or β-keto aldehyde moiety-comprising compound is used as the catalyst which has a melting point of less than 500° C., more preferably of less than 400° C., and most preferably of less than 300° C. Preferably, said catalyst has a boiling point higher than 120° C. in order to reduce the amount of catalyst that will end up in the isolated halogenated product.

The organic compound according to the present invention to be halogenated with one or both hydroxyl groups comprises at least one vicinal diol moiety. By the term vicinal diol moiety is meant that the organic compound comprises at least two hydroxyl groups in a vicinal position in relation to each other, i.e. the hydroxyl groups are attached to adjacent carbon atoms. The OH groups can be primary, secondary, or tertiary OH functionalities. Said compounds may comprise, besides the vicinal diol functionality, heteroatoms such as a halide, sulphur, phosphorus, nitrogen, oxygen, silicon, boron, or combinations thereof. Preferably, the organic compound which is to be halogenated according to the present invention is a liquid at the reaction temperature.

Preferred examples of organic compounds which are suitable for halogenation according to the present process include 1,2-ethanediol, 1,2-propanediol, 1,2,4-butanetriol, 1,2-pentanediol, 1,2-hexanediol, and glycerol.

In a particularly preferred embodiment of the present invention, glycerol (1,2,3,-propanetriol) is halogenated. In this case, preferably, glycerol is used which has been obtained as a byproduct in the production of biodiesel or during conversions of fats or oils of plant or animal origin in general, such as saponification, trans-esterification or hydrolysis reactions. Halogenated products produced from glycerol, i.e. dichlorohydrins or dibromohydrins, are preferably used in conventional processes to produce epichlorohydrin and epibromohydrin, respectively, in the presence of a base. The preparation of epichlorohydrin can take place as described for example in *Organic Syntheses, Coll. Vol.* 2, p. 256, Vol. 16, pages 30-31 or in DE 1 075 103.

The hydrogen halide can be used in the form of an aqueous solution or as gaseous hydrogen halide. The use of gaseous hydrogen halide is most preferred. The hydrogen halide used in the process according to the present invention preferably is hydrogen bromide or hydrogen chloride. Hydrogen chloride is most preferred. Although the application of pure hydrochloric acid (>99% pure) is preferred, a person skilled in the art will realize that the process according to the present invention is particularly suitable for application of raw materials with only limited purity, e.g. HCl produced as a byproduct from a chemical production process.

In one embodiment of the process according to the present invention, the organic compound comprising at least one vicinal diol moiety is placed in a closed reaction vessel, heated, and pressurized under an atmosphere of hydrogen halide gas in the presence of the catalyst comprising a β-diketone moiety. The present invention may include various process schemes. Thus the process can be carried out in a batch reactor, preferably in fed-batch operation, or in a continuously operating system such as in a cascade of continuous flow reactors of the liquid gas type.

In an exemplifying batch process, the organic compound comprising at least one vicinal diol moiety which is to be halogenated and the catalyst comprising a β-diketone moiety are charged to a reaction vessel. Gaseous hydrogen halide is then added to the desired pressure, and the reaction mixture is heated to the desired temperature for the desired length of time. The reaction mixture is then discharged from the reaction vessel and either purified or sent to other equipment for further processing, or to storage.

In an illustrative fed-batch process, one or more of the reagents are fed to a reaction vessel over a period of time throughout the reaction while other reagents are fed only at the start of the reaction. In such a process, for example, the organic compound comprising at least one vicinal diol moiety and the catalyst comprising a β-diketone moiety may be fed in a single batch to a halogenation reactor, which is then held at reaction conditions for a suitable time, while a hydrogen halide gas is fed continuously throughout the reaction at the desired rate, which may be at constant flow, or constant pressure. After the reaction, the hydrogen halide feed can be terminated, and the reactor contents can be discharged for storage, purification or further processing.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing. In such a scheme, the organic compound comprising at least one vicinal diol moiety and the catalyst comprising a β-diketone moiety may be fed to the equipment and hydrogen halide gas added as desired at a single point or at multiple points throughout the process equipment, which may include continuously stirred tank reactors, tubes, pipes or combinations thereof.

In a continuous recycle process, one or more of the unreacted starting material, reaction intermediates, hydrogen halide, or the catalyst according to the present invention exiting from the process equipment are recycled back to a point earlier in the process. In this manner, raw material efficiencies are maximized and/or catalysts reused. Since catalysts are reused in such a process scheme, it may be desirable to employ the catalysts in a higher concentration than is the case in a single-pass process, where they are often discarded. This may result in faster reactions, or in smaller process equipment, which results in lower capital costs for the equipment employed.

The total mean residence time of the reaction mixture in the reactor typically is at least 15 minutes, preferably at least 2 hours, and most preferably at least 4 hours. Typically, the total mean residence time is less than 24 hours, more preferably less than 18 hours, most preferably less than 12 hours.

International patent applications WO 2006/020234 and WO 2005/054167 show detailed examples of suitable equipment for carrying out the process according to the present invention.

The catalyst according to the present invention can be introduced into the reaction vessel neat, or as a solution in one of the reactants, e.g. glycerol, or in an appropriate organic solvent. Suitable organic solvents include alcohols and esters. The addition of the catalyst can be performed continuously or discontinuously. The catalyst according to the present invention is typically used in an amount of at least 0.05% by weight, more preferably at least 0.5% by weight, and most preferably at least 1% by weight, based on the total weight of the liquid reaction mixture. Preferably, no more than 50% by weight, more preferably no more than 25% by weight, and most preferably no more than 15% by weight of catalyst is employed, based on the total weight of the liquid reaction mixture.

The organic compound comprising at least one vicinal diol moiety can be contacted with the hydrogen halide gas in any conventional manner. For example, it can be added through nozzles, perforated plates or pipes, microporous plates, and ejectors. Typically, for each mole of hydroxyl groups to be halogenated, at least 1 mole, more preferably at least 1.1 moles, and even more preferably at least 1.2 moles of hydrogen halide gas are added. Typically, no more than 10 moles, preferably no more than 5 moles, and most preferably no more than 3 moles of hydrogen halide gas are added for each mole of hydroxyl groups to be halogenated. As the skilled person will understand, if the process is operated by circulating at least part of the reaction mixture, it is possible to use less than 1 mole of hydrogen halide gas for each mole of hydroxyl groups to be halogenated.

It may be preferred to purify the organic compound which is to be halogenated before it is employed in the halogenation reaction by removing contaminants, e.g. water, organic contaminations or inorganic contaminations, before use. The purification can be performed using purification techniques well known in the art, such as distillation, extraction, absorption, centrifugation, or other appropriate methods.

Recovery of the halogenated product can be achieved in a variety of ways. It is preferably achieved by distillation or evaporation, preferably in a continuous fashion, either directly from the reaction vessel or from a separate piece of equipment such as a vaporizer or a distillation column. Alternatively, the halogenated product can be isolated via liquid extraction or absorption.

To achieve higher conversions, it might be advisable to remove at least part of the water produced during the reaction. This can for example be achieved via distillation under reduced pressure. For this purpose, use may be made of any conventionally employed device for distillation, such as evaporators of various constructions with or without a source of heat, rectification columns with various internals such as trays, structured packing, random packing, etc.

The process according to the present invention is typically carried out at a temperature of at least 20° C., more preferably at least 40° C., even more preferably at least 60° C., and most preferably at least 80° C. The temperature preferably is at most 160° C., more preferably at most 150° C., even more preferably at most 140° C.

The process is preferably carried out at a pressure of at least 0.3 bar, preferably at least 0.5 bar, since reduced pressure will have a negative effect on the overall reaction rate Preferably, the pressure is not higher than 10 bar, more preferably not higher than 5 bar, and most preferably not higher than 3 bar. Most preferably, the halogenation process is carried out at atmospheric pressure.

With the present process, significantly lower amounts of catalyst end up in the product as compared to processes wherein prior art catalysts such as acetone are used, and often traces of catalyst cannot be detected at all.

In one embodiment according to the invention, glycerol is used as the organic compound which is chlorinated. The monochlorohydrin produced is preferably used to prepare glycidol by bringing it into contact with a base. Such a process is described for example in WO 2009/016149. The dichlorohydrin (often a mixture of 2,3-dichloropropan-1-ol and 1,3-dichloropropan-2-ol) produced is preferably used to prepare epichlorohydrin by bringing it into contact with a base. Such a process is described for example in *Organic Syntheses, Coll. Vol.* 2, p. 256 (1957); *Organic Syntheses, Coll. Vol.* 1, p. 233 (1958); GB 2173496; U.S. Pat. No. 4,496, 753; US 2008/0015369; US 2008/0015370; US 2008/0045728; or EP 1 059 278.

In another embodiment according to the invention, 1,2 ethanediol is used as the organic compound which is chlorinated to produce chloroethanol. Ethylene oxide can be prepared by bringing the chloroethanol into contact with a base (see for example Kirk-Othmer Encyclopedia of Chemical Technology, Third Edition, Vol. 9, John Wiley & Sons (1980), p. 432-471; Wurtz, A. (1859). *Compt. rend.* 48: 101-104; P. P. McClellan (1950). "Manufacture and Uses of Ethylene Oxide and Ethylene Glycol". *Ind. Eng. Chem.* 42: 2402-2407).

In yet another embodiment according to the invention, 1,2-propanediol is used as the organic compound which is chlorinated to produce chloropropanol. Typically, a mixture of 1-chloro-2-propanol and 2-chloro-1-propanol is obtained, with 1-chloro-2-propanol being the major part. Propylene oxide can be prepared by bringing the chloropropanol into contact with a base. Such a process is described for example in *Organic Syntheses, Coll. Vol.* 8, p. 434 (1993); Vol. 66, p. 160 (1988); and Kirk-Othmer Encyclopedia of Chemical Technology, Third Edition, Vol. 19, John Wiley & Sons (1982), p. 246-274).

The process according to the present invention is further illustrated by the following examples.

EXAMPLES 1-3 AND COMPARATIVE EXAMPLES A-C

The following screening test was used to assess the catalytic activity. A small vial was filled with a mixture of glycerol (ex J. T. Baker) and hydrochloric acid (36-38% aqueous solution, ex J. T. Baker). A typical mixture consisted of 15 wt % of glycerol and 85 wt % of hydrochloric acid solution. To the vial a catalyst was added, in an amount of about 0.2 to 10 grams of mixture. The vial was subsequently heated to 60-70° C. and kept at that temperature for 60-80 hours. The organic composition was analyzed by HPLC. The catalytic activity was evaluated as the relative amount of dichloropropanol (DCH) formed in the test vial compared to the DCH formed in a blank test-vial, i.e. without addition of a catalyst. 2,3-Pentanedione (ex Acros), 1,3-cyclohexanedione (ex Aldrich), and 3,5-heptanedione (ex Aldrich) were used in Examples 1, 2, and 3, respectively. The results are summarized in Table 1 and compared to the results obtained using no catalyst (Comparative Example A), acetone (Comparative Example B), and methyl ethyl ketone (Comparative Example C) (acetone and MEK ex Fluka).

As can be derived from Table 1, the catalysts according to the invention demonstrate improved catalytic activity compared to the monoketones such as acetone and MEK. Further, a good selectivity towards DCH is observed.

TABLE 1

| Example | Catalyst | catalyst fraction [wt %] | mol fraction [mol %] | | |
|---|---|---|---|---|---|
| | | | glycerol | MCH | DCH |
| A | none | | 98.2% | 1.8% | 0.0% |
| B | acetone | 2.3% | 56.3% | 41.8% | 1.9% |
| C | methyl ethyl ketone (MEK) | 2.9% | 68.8% | 30.4% | 0.8% |
| 1 | 2,4-pentanedione | 3.5% | 15.5% | 71.3% | 13.2% |
| 2 | 1,3-cyclohexanedione | 2.8% | 15.6% | 68.8% | 15.6% |
| 3 | 3,5-heptanedione | 2.9% | 12.7% | 69.4% | 17.8% |

The invention claimed is:

1. A process for the catalytic halogenation of an organic compound having at least one vicinal diol moiety, said process comprising bringing the organic compound having at least one vicinal diol moiety into contact with a hydrogen halide in the presence of a catalyst, wherein the catalyst is an organic compound having a β-diketone moiety or a β-keto aldehyde moiety.

2. The process according to claim 1 wherein the catalyst is an organic compound having a β-diketone moiety.

3. The process according to claim 2 wherein the catalyst is selected from the group consisting of 2,4-pentanedione, 1-phenyl-1,3-butanedione, dibenzoylmethane, 3,5-heptanedione, 1,3-cyclopentanedione, 2,4-hexanedione, 1,3-cyclohexanedione, triacetylmethane, 1,1,2-triacetylethane, 2,4,6-heptanetrione, 1,3,5-cyclohexanetrione, and 1,1,2,2-tetraacetylethane.

4. The process according to claim 1 wherein the organic compound having at least one vicinal diol moiety is selected from the group consisting of 1,2-ethanediol, 1,2-propanediol, 1,2,4-butanetriol, 1,2-pentanediol, 1,2-hexanediol, and glycerol.

5. The process according to claim 1 wherein the hydrogen halide is hydrogen chloride.

6. The process according to claim 5 wherein the hydrogen chloride is gaseous hydrogen chloride.

7. The process according to claim 1 wherein for each mole of hydroxyl groups to be halogenated, between 1 and 10 moles of hydrogen halide are added.

8. The process according to claim 1 wherein the process is carried out at a temperature of between 20° and 160° C.

9. The process according to claim 1 wherein the organic compound having at least one vicinal diol moiety is glycerol and the hydrogen halide is gaseous hydrogen chloride.

10. The process according to claim 9, further comprising preparing monochlorohydrin which is subsequently used to prepare glycidol by bringing the monochlorohydrin into contact with a base.

11. The process according to claim 9, further comprising preparing dichlorohydrin which is subsequently used to prepare epichlorohydrin by bringing the dichlorohydrin into contact with a base.

12. The process according to claim 1 wherein the organic compound having at least one vicinal diol moiety is 1,2-ethanediol or 1,2-propanediol and the hydrogen halide is gaseous hydrogen chloride.

13. The process according to claim 12 wherein the resulting chloroethanol or chloropropanol is subsequently used to prepare ethylene oxide or propylene oxide, respectively, by bringing the chloroethanol or chloropropanol, respectively into contact with a base.

14. The process according to claim 3 wherein the organic compound having at least one vicinal diol moiety is selected from the group consisting of 1,2-ethanediol, 1,2-propanediol, 1,2,4-butanetriol, 1,2-pentanediol, 1,2-hexanediol, and glycerol.

15. The process according to claim 3 wherein the hydrogen halide is hydrogen chloride.

16. The process according to claim 14 wherein the hydrogen halide is hydrogen chloride.

17. The process according to claim 16 wherein the hydrogen chloride is gaseous hydrogen chloride.

18. The process according to claim 3 wherein the organic compound having at least one vicinal diol moiety is glycerol and the hydrogen halide is gaseous hydrogen chloride.

19. The process according to claim 3 wherein the organic compound having at least one vicinal diol moiety is 1,2-ethanediol or 1,2-propanediol and the hydrogen halide is gaseous hydrogen chloride.

20. The process according to claim 8 wherein the organic compound having at least one vicinal diol moiety is 1,2-ethanediol or 1,2-propanediol and the hydrogen halide is gaseous hydrogen chloride.

\* \* \* \* \*

UNITED STATES PATENT AND TRADEMARK OFFICE
CERTIFICATE OF CORRECTION

PATENT NO.       : 8,558,021 B2                              Page 1 of 1
APPLICATION NO.  : 13/256353
DATED            : October 15, 2013
INVENTOR(S)      : Ten Kate et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 106 days.

Signed and Sealed this

Fifteenth Day of September, 2015

Michelle K. Lee
*Director of the United States Patent and Trademark Office*